United States Patent [19]
Desu et al.

[11] Patent Number: 5,348,631
[45] Date of Patent: Sep. 20, 1994

[54] METHOD AND APPARATUS FOR SYNTHESIZING LEAD β-DIKETONATES

[75] Inventors: Seshu B. Desu, Blacksburg, Va.; May Nyman, Albuquerque, N. Mex.; Pradyot A. Agaskar, Lawrenceville, N.J.

[73] Assignee: Sharp Kabushiki Kaisha, Osaka, Japan

[21] Appl. No.: 73,113

[22] Filed: Jun. 7, 1993

[51] Int. Cl.$^5$ ............................................. C01G 21/00
[52] U.S. Cl. ............................ 204/157.4; 204/157.42; 204/157.62; 204/157.93; 556/40; 556/81
[58] Field of Search ................ 204/157.42, 157.62, 204/157.93, 157.4; 556/40, 81

[56] References Cited

U.S. PATENT DOCUMENTS

3,245,892  9/1960  Jones ........................... 204/157.42
3,351,539  4/1965  Branson ....................... 204/157.42

Primary Examiner—John Niebling
Assistant Examiner—Cybille Delacroix-Muirheid
Attorney, Agent, or Firm—Beaton & Swanson

[57] ABSTRACT

A method and apparatus for the synthesis of β-diketonates such as Pb(fod)$_2$ and Pb(thd)$_2$ for use as precursors in metalorganic chemical vapor deposition processes. Lead oxide and a medium of pentane and a protonated ligand (H-fod or H-thd) are combined in a flask and subjected to reaction-promoting ultrasonic waves. The flask is immersed in a water bath to maintain a constant cool temperature, and the flask may include one or more arms for cooling and circulation of the medium during the reaction.

10 Claims, 6 Drawing Sheets

FIG. 8

METHOD AND APPARATUS FOR SYNTHESIZING LEAD β-DIKETONATES

This invention was made with Government support under Grant N00014-90-J-1957 awarded by the Department of Navy. The Government has certain rights in the invention.

FIELD OF THE INVENTION

The present invention relates to a method and apparatus for synthesizing lead β-diketonates, including lead bis-heptafluorodimethyloctadione (Pb(fod)$_2$) and lead bis-tetramethylheptadione (Pb(thd)$_2$) for use especially as a precursor in Metal Organic Chemical Vapor Deposition (MOCVD).

BACKGROUND OF THE INVENTION

A variety of techniques have been used for the deposition of ferroelectric thin films. In general, the thin film deposition techniques can be divided into two major categories: (1) physical vapor deposition (PVD) and (2) chemical processes. Among the PVD techniques, the most common methods used for the deposition of ferroelectric thin films are electron beam evaporation, rf diode sputtering, rf magnetron sputtering, dc magnetron sputtering, ion beam sputtering, molecular beam epitaxy (MBE), and laser ablation. The chemical processes can be further divided into two subgroups, i.e., chemical vapor deposition (CVD), and wet chemical processes including sol-gel process and metalorganic decomposition (MOD).

The PVD techniques require a high vacuum, usually better than $10^{-5}$ torr, in order to obtain a sufficient flux of atoms or ions capable of depositing onto a substrate. The advantages of the PVD techniques are (1) dry processing, (2) high purity and cleanliness, and (3) compatibility with semiconductor integrated circuit processing. However, these are offset by disadvantages such as (1) low throughput, (2) low deposition rate, (3) difficult stoichiometry control, (4) high temperature post-deposition annealing, and (5) high equipment costs.

Laser ablation is a newly developed thin film deposition technique and the understanding of this process is in its infant period. Laser ablation has found some success in depositing high temperature superconducting films. The major problems of this technique are the composition and thickness non-uniformity of the deposited films over a large scale.

The wet chemical processes include MOD and sol-gel process. The advantages of the wet chemical process are (1) molecular homogeneity, (2) high deposition rate and high throughput, (3) excellent composition control, (4) easy introduction of dopants, and (5) low capital cost, since deposition can be done in ambient condition and so no vacuum processing is needed. The major problems due to this wet process are (1) film cracking during the post-annealing process and (2) possible contamination which results in difficulty in incorporating this technique into semiconductor processing. However, because it provides a fast and easy way to produce the complex oxide thin films, this wet chemical process has a very important role in the investigation of the interrelationship among the processing, the microstructure, and the property of the films.

Of all the above mentioned techniques, the metalorganic chemical vapor deposition (MOCVD) technique appears to be one of the most promising because it offers advantages of simplified apparatus, excellent film uniformity, composition control, high film densities, high deposition rates, excellent step coverage, and amenability to large scale processing. The excellent film step coverage that can be obtained by MOCVD cannot be equaled by any other technique. Purity, controllability, and precision that have been demonstrated by MOCVD are competitive with the MBE technique. More importantly, novel structures can be grown easily and precisely. MOCVD is capable of producing materials for an entire class of devices which utilize either ultra-thin layers or atomically sharp interfaces. In addition, different compositions can be fabricated using the same sources.

The first successful deposition of oxide-based ferroelectric thin films by CVD was reported by Nakagawa, et al. in "Preparation of PbTiO$_3$ ferroelectric thin film by chemical vapor deposition," *Jpn. J. Appl. Phys.*, 21(1), L655 (1982). They deposited PbTiO$_3$ films on Pt-coated silicon wafers by using TiCl$_4$, PbCl$_2$, O$_2$, and H$_2$O as source materials. Several problems arose from their studies: (1) very high evaporation temperature (700° C.) was required of PbCl$_2$, (2) poor ferroelectric properties ($P_r = 0.16$ μC/cm$^2$ and $E_c = 14.5$ kV/cm), (3) poor composition uniformity in the bulk of PbTiO$_3$ films, and (4) crystallographic imperfections due to water and/or chloride contamination. Obviously, chlorides are not ideal precursors for the CVD process. In general, metalorganic precursors have relatively high vapor pressures at lower temperatures. By carefully selecting the organic compounds, the undesirable contaminations in the films can be completely excluded. Metalorganic compounds are now used almost exclusively for the deposition of oxide thin films.

One of the challenges in MOCVD is the choice and synthesis of the precursors. Precursors for MOCVD are chosen on the basis of their ability to satisfy several requirements, including: sufficient vapor pressure at low temperatures, thermal stability at vaporization temperature, rapid decomposition with minimal ligand contamination at low substrate temperatures, stability under ambient conditions, and minimal toxicity.

Vapor pressure of 0.1–0.5 torr at a vaporization temperature of less than 170° C. is necessary for effective deposition; low vaporization temperature provides efficiency of heating. Efficient transportation of the precursor from the bubbler to the substrate necessitates stability to prolonged heating in vacuo at the vaporization temperature. Thermal stability ensures minimal decomposition or intermediate reactions in the bubbler, or in gas phase before contacting the substrate. Low deposition temperatures of 350°–500° C. ensure minimal film-substrate interactions, and efficiency of heating. The decomposition of precursors at these temperatures should be rapid and clean, with minimal contamination from organic constituents of the ligands such as hydrogen, carbon or fluorine. Finally, a precursor's stability to oxygen and moisture, and its non-toxicity are necessary for ease of handling. Hygroscopic, air sensitive or toxic precursors require special closed chambers for transportation and storage. Additionally, hydration or oxidation can render the precursor nonreactive.

Classes of useful precursors for MOCVD of PbO include: (1) lead alkyls, (2) lead alkoxides, and (3) lead β-diketonates. The high volatility of the liquid lead alkyls such tetraethyl lead and lead alkoxides such as lead ethoxide, decreases ease of handling due to the extreme toxicity of these compounds. Additionally alkoxides are extremely sensitive to moisture, and consequently decompose via autohydrolysis.

An alternative of precursors is the lead β-diketonates. Several precursor requirements are fulfilled by the lead β-diketonates: they are not volatile at room temperature and are therefore less toxic than the alkyls and alkoxides, they have sufficient vapor pressure of 0.1–0.5 torr below 200° C., and they decompose at temperatures less than 500° C. See R. E. Sievers and J. W. Connolly, "Tris (1, 1, 1, 2, 2, 3, 3-Heptafluoro-7, 7-dimethyl-4, 6-octadionato) Iron (III) and Related Complexes", *Inorganic Synthesis*, 12, XII, p. 72–77 (1969). Lead β-diketonates are of the form:

The $R_1$ and $R_2$ groups are alkyl or fluorinated alkyl groups. The properties of the different lead β-diketonate species are a function of the nature of the R-substituents. For instance, lead acetylacetonate ($R_1 = R_2 = CH_3$) is stable to air and moisture. Volatility is also a function of the nature of the R-group; lead acetylacetonate has 1 torr vapor pressure at 95° C., lead trifluoroacetylacetonate ($R_1 = CH_3$, $R_2 = CF_3$) has 1 torr vapor pressure at 72° C., and lead hexafluoroacetylacetonate ($R_1 = R_2 = CF_3$) has 1 torr vapor pressure at 67° C.[4]. Additionally, the R-substituents affect the strength of the metal-oxygen bond; consequently, decomposition temperature is a function of the R-group. This phenomenon is discussed for Cu and Fe β-diketonates with various R-substituents in C. Reichert and J. B. Westmore, "Mass Spectral Studies of Metal Chelates, VI, Mass Spectra and Appearance Potentials of β-diketonates of Copper (II)", *Canadian Journal of Chemistry*, 48, pp. 3213–3222 (1970), and H. F. Holtzclaw, R. L. Lintvedt, H. E. Baumgarten, R. G. Parker, M. M. Bursey, P. F. Rogerson, "Mass Spectra of Metal Chelates, I, Substituent Effects on Ionization Potentials and Fragmentation Patterns of some 1-methyl-3-alkyl-1, 3-dione Copper (II) Chelates", *Journal of the American Chemical Society*, 91, 14, pp. 3774–3778.

Lead bis-heptafluorodimethyloctadione, or Pb(fod)$_2$, is a lead β-diketonate which is potentially a useful precursor for MOCVD of PbO; it has been deposited at 450°–600° C. See D. C. Bradley, "Metal Alkoxides as Precursors for Electronic and Ceramic Materials", *Chemical Reviews*, 89, 6, pp. 1317–1322 (1989). The R-substituents for Pb(fod)$_2$ are $R_1 = C_3F_7$ and $R_2 = C(CH_3)_3$, it has sufficient vapor pressure of 1 torr at 95°–105° C., and it is stable to air and moisture. See R. C. Mehrotra, R. Bohra, D. P. Gaur, "Metal β-diketonates and Allied Derivatives, Chapter 2", *Academic Press, Inc.*, New York, NY, 1978. A similar compound is lead bis-tetramethylheptadione, or Pb (thd)$_2$. The two compounds, Pb(fod)$_2$ and Pb(thd)$_2$ differ only by substituents on their respective ligands. Properties such as volatility, thermal stability, moisture stability and temperature of decomposition differ as a function of the substituents. Pb(fod)$_2$ has a vapor pressure of 1 torr at 98° C. while Pb(thd)$_2$ has a vapor pressure of 1 torr at 60° C. Both are relatively stable and safe for handling under ambient conditions. See G. K. Schwitzer, B. P. Pullen and Y. Fang, *Anal. Chim. Acta*, 43, 332–334 (1968).

References on MOCVD using β-diketonates include U.S. Pat. No. 5,096,737 by Baum, et al. and U.S. Pat. No. 5,045,348 by Brierley, et al.

SUMMARY OF THE INVENTION

The present invention is a method and apparatus for synthesizing lead β-diketonates such as Pb(fod)$_2$ and Pb(thd)$_2$ for use as a precursor in MOCVD. Lead oxide powder is combined with a stoichiometric excess of protonated ligand (H-fod or H-thd) and an equal volume of toluene in a flask. The flask is submerged in an ultrasonic bath at room temperature. The flask medium is subjected to ultrasonic waves to produce cavitation within the flask and resulting shock waves in the reaction medium. It is believed that the ultrasonic cavitation and resulting shock waves assist the reaction by dispersing the lead oxide powder and perhaps producing activated free radicals such as fod$^-$ and thd$^-$. The flask is open at the top to receive the ultrasonic probe and has a set of side arms at the bottom to assist in circulating the medium and cooling the medium by thermal conductivity with the bath.

DETAIL DESCRIPTION OF THE INVENTION

Figure 1:
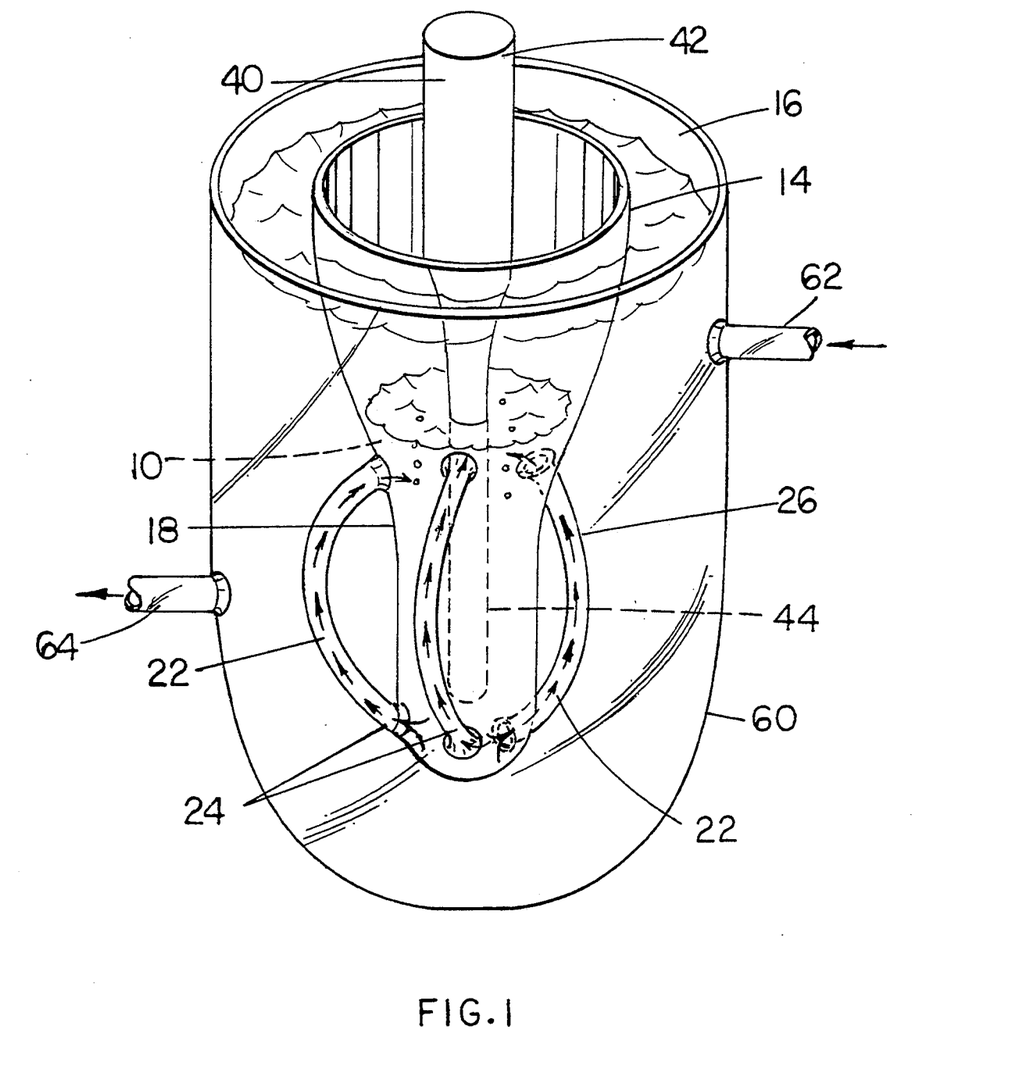
FIG. 1 is a schematic diagram of an apparatus in accordance with the present invention.

In a preferred embodiment of the invention, 10 ml of pentane and 6 mL of fod ligand are mixed in a 50 mL round-bottom flask. The flask 14 preferably has a configuration as shown in FIG. 1, with an open mouth 16 at the top and a tapered bottom 18. In the vicinity of the bottom are a set (three in the embodiment shown) of side arms 22 having the function described below. Each side arm 22 is a conduit with a bottom opening 24 in communication with the bottom of the flask 14 and a top opening 26 in communication with the flask 14 above the flask bottom.

An ultrasonic probe 40 is positioned in the flask 14 so that the top 42 extends out of the flask mouth 16 and the probe head 44 is just above the bottom of the flask 14 and submerged in the medium 10. The probe 40 is 1500 watts in the preferred embodiment. The flask 14 with the probe 40 positioned therein is suspended in a water bath in a water jacket 60. The water jacket 60 has an inlet 62 toward the top and an outlet 64 toward the bottom.

In operation, the flask 14 is positioned in the water jacket 60 and the probe 40 is positioned in the flask 14 as shown in FIG. 1. Pentane and fod are added to the flask, and the ultrasonic probe is activated. (Essentially, the same process can be used to produce Pb(thd)$_2$ as is used to produce Pb(fod)$_2$, but the protonated ligand is H-thd rather than H-fod.) Two grams of lead (II) oxide is slowly added to the medium. As the reaction proceeds, the lead oxide disappears, and a yellow oily layer containing unreacted fod, Pb(fod)$_2$ and pentane, and a water layer, are formed. The pentane decreases the viscosity of the yellow oily layer so that the lead oxide can be dispersed by the ultrasonic energy to react with the fod. Pentane was chosen for this function because it is non-complexing, inexpensive, relatively nontoxic, and easily removed from the product due to its high volatility at room temperature and pressure.

As the reaction takes place, the medium circulates from the bottom of the flask 14, into the bottom openings 24 of the side arms 22, up through the side arms 22 and out the top openings 26 of the side arms 22 and back into the main body of the flask 14. At the same time, sufficient water is flowed into the water jacket 60 through the inlet 62 and out the outlet 64, to maintain the water temperature at ambient. The water in the water jacket draws heat away from the medium, primarily by thermal conductivity from the medium through the side arms 22 and into the water.

In order to remove the unreacted fod, pentane and water, the product mixture is heated in vacuo at 50° C. (vaporization temperature of fod at reduced pressure) for 10-20 hours. After vacuum treatment, yellow powder remains, which can be analyzed for Pb(fod)$_2$ content. Water and pentane are easily removed due to immiscibility with fod and Pb(fod)$_2$, and high volatility, respectively. Complete removal of pentane and water may be confirmed by proton nuclear magnetic resonance spectroscopy (NMR). The unreacted fod is more difficult to remove from Pb(fod)$_2$ due to the solubility of the Pb(fod)$_2$ in the fod. By comparing some properties of fod to the properties of the Pb(fod)$_2$, the purity of the Pb(fod)$_2$ can be determined. Purity analyses may include: (1) melting point determination, (2) carbon and hydrogen elemental analysis, (3) mass spectral evaporation profiles and (4) proton NMR spectroscopy.

By comparing the melting point of the synthesized and purified Pb(fod)$_2$ to reported melting points (2, 7, 8), the purity can be estimated. As shown in Table 1 below, it was found for the example above that the presence of free fod ligand decreases the melting point of Pb(fod)$_2$ significantly. For instance, the melting point is decreased by almost 20° C. in a sample containing 50% free fod and 50% Pb(fod)$_2$. The synthesized and purified Pb(fod)$_2$ has a melting point within the range of various reported values, which suggests it is pure.

TABLE 1

| Melting Point at 1 atm | |
| --- | --- |
| Reported | Found |
| 72° C. | pure Pb(fod)$_2$ |
|  | 73-76° C. |
| 74-75.1° C. | 50% Pb(fod)$_2$ |
|  | 50% fod |
| 74° C. | 55-60° C. |

Table 2 shows the calculated values of carbon and hydrogen weight percents of fod and Pb(fod)$_2$, which were determined experimentally by combustion. The carbon and hydrogen weight percents of the synthesized and purified Pb(fod)$_2$ agree with the calculated values within experimental error.

TABLE 2

| | Elemental Analysis | | |
| --- | --- | --- | --- |
| | wt % calculated | | wt % found |
| | Pb(fod)$_2$ | fod | Pb(fod)$_2$ |
| Carbon | 30.11 | 40.54 | 29.26 |
| Hydrogen | 2.51 | 3.72 | 2.40 |

Figure 2:
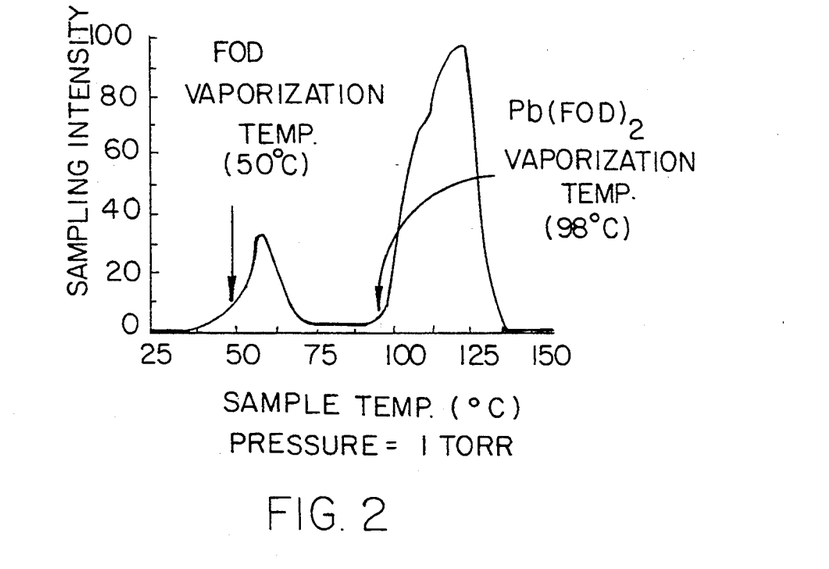
FIG. 2 is an evaporation profile for samples containing Pb(fod)$_2$ and free fod.
Figure 3:
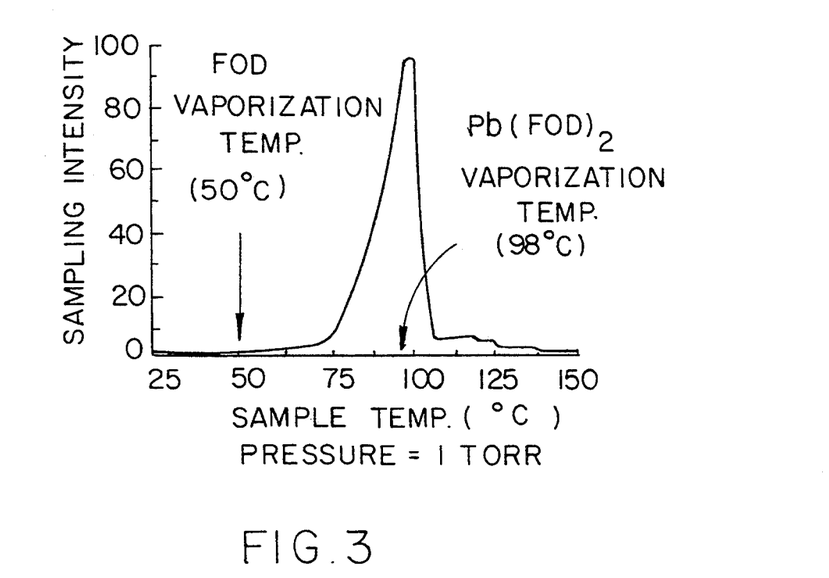
FIG. 3 is an evaporation profile for samples containing purified Pb(fod)$_2$.

The evaporation profiles shown in FIGS. 2 and 3 were recorded during the heating of samples containing Pb(fod)$_2$ and free fod, and purified Pb(fod)$_2$, respectively. The graphs record the relative concentrations of sample evaporated into the probe as it is heated to 150° C. Maximum sampling intensity is defined as 100%. Any pure sample should exhibit a sharp peak centered at its evaporation temperature at 1 torr. The sample containing free fod ligand and Pb(fod)$_2$ exhibits two peaks; one centered around 60° C., and one at 115° C. The purified Pb(fod)$_2$ heating profile exhibits a sharp peak centered around 98° C. This temperature is within the reported range. The heating profile of purified Pb(fod)$_2$ shows no sampling at the vaporization temperature of free fod (50° C.) at 1 torr.

Figure 4:
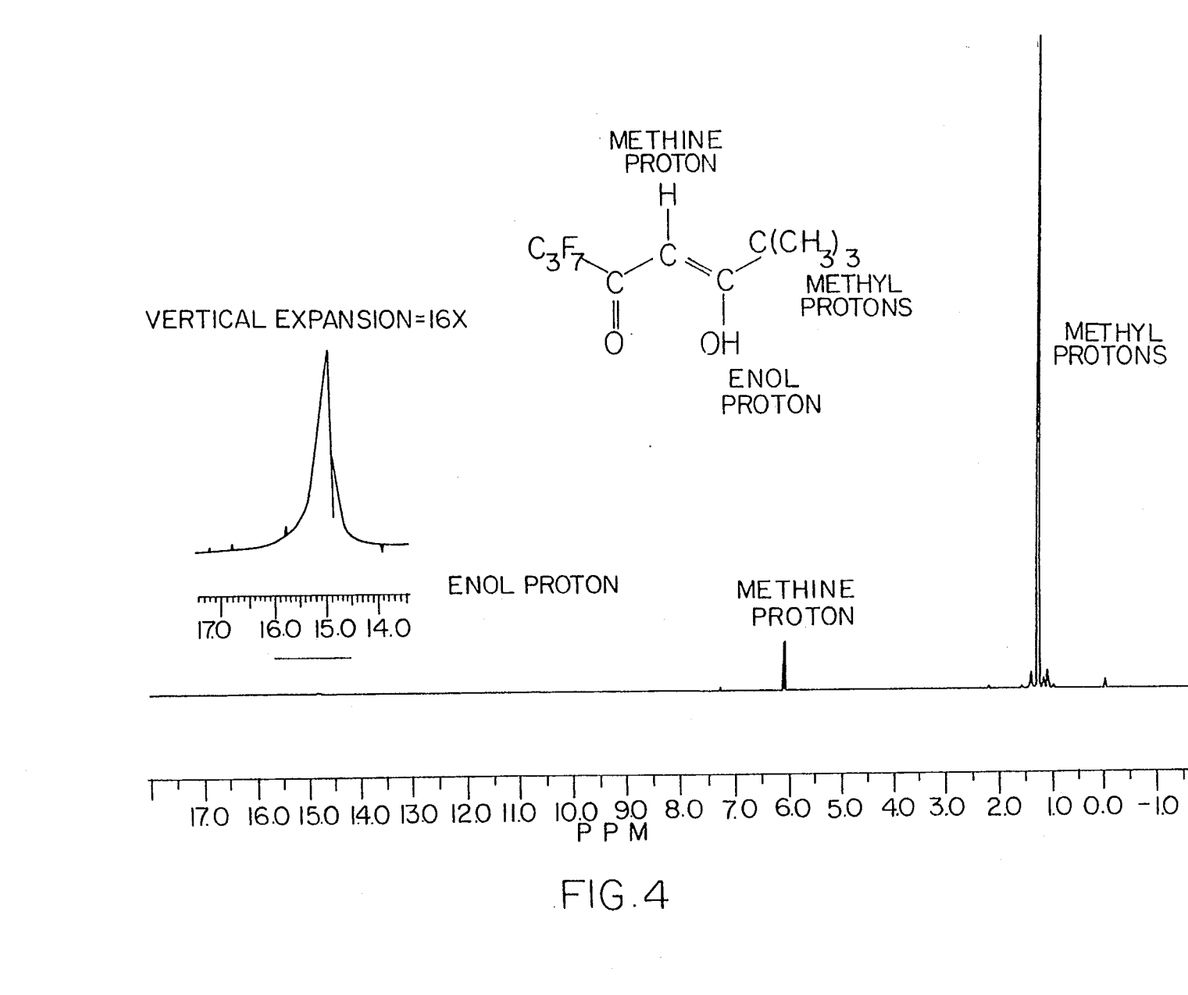
FIG. 4 is an NMR spectrum of free fod.
Figure 5:
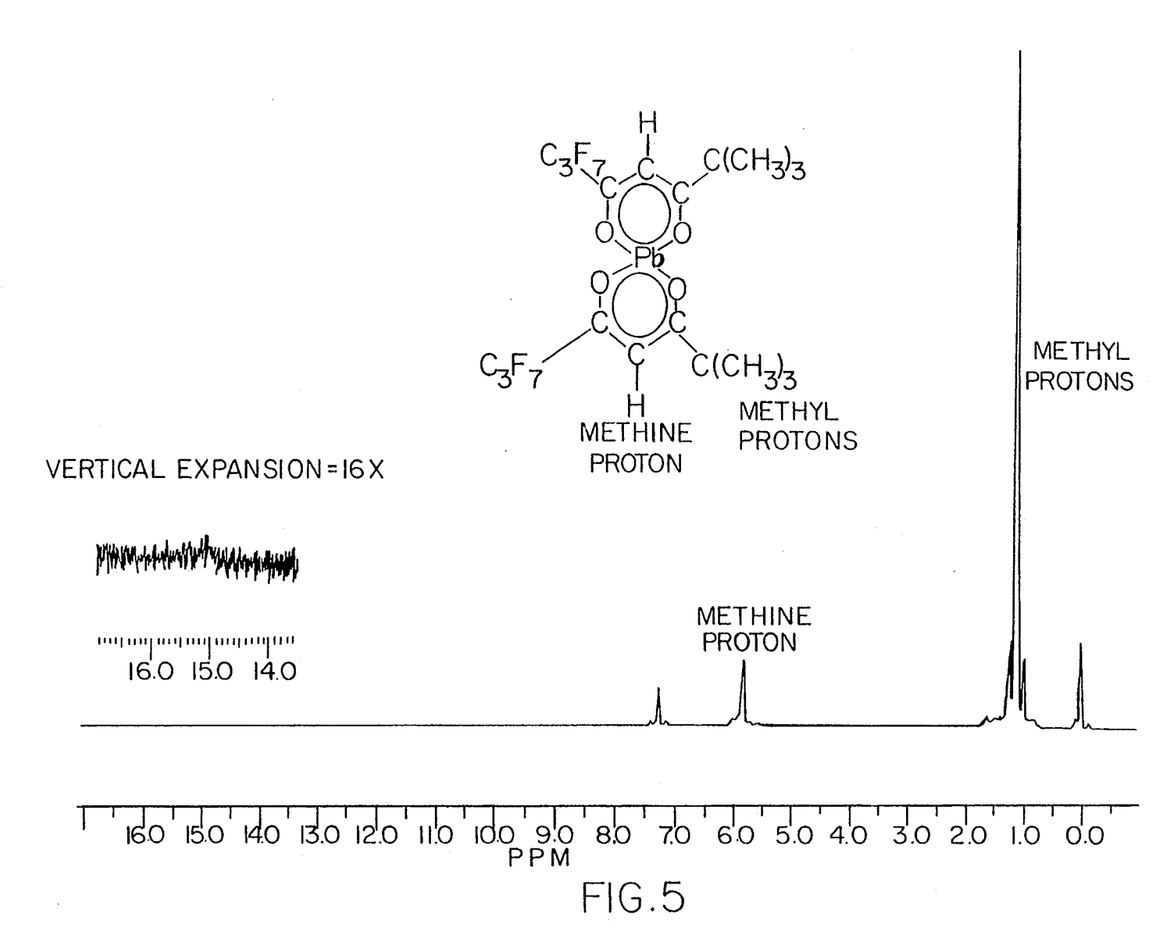
FIG. 5 is an NMR spectrum of Pb(fod)$_2$.

The proton NMR spectrum of free fod shows three distinct peaks (FIG. 4): the methine peak at 6.0774 ppm, the methyl peak at 1.2272 ppm and the enol peak at 14.9805 ppm. The methine and methyl peaks shift slightly upfield to 5.8166 ppm and 1.1391 ppm, respectively upon complexing the $\beta$-diketonate ligand (fod) with the metal (lead) (FIG. 5). When the enol proton is replaced by lead to form the metal complex, the enol peak should disappear, if free fod were present in the Pb(fod)$_2$, a remnant enol peak would be visible in the Pb(fod)$_2$ spectrum. As was expected for a NMR spectrum of pure Pb(fod)$_2$, no enol peak was observed (FIG. 5).

Characterization of decomposition and volatility properties of Pb(fod)$_2$ can be helpful in determining its suitability for MOCVD of PbO by exploring the following questions: (1) does Pb(fod)$_2$ fulfill the requirements for precursor suitability for MOCVD and (2) what conditions (i.e. vaporization temperature, and decomposition temperature) are necessary for high quality film growth? The decomposition studies were carried out in 140 mL quartz tubes backfilled with 425 torr O$_2$ on a standard Schlenk line, and sealed with a propane torch. Each decomposition experiment was run with 0.1 g Pb(fod)$_2$. Decomposition time was also kept constant at 30 min, and decomposition experiments were performed at 350° C., 400° C. and 450° C. The oxygen present in the sealed tube was 1.37 x the stoichiometric amount necessary for all the Pb(fod)$_2$ to decompose to PbO. Additionally, 0.2 Ml H$_2$O was added to the Pb(fod)$_2$ to displace the fluorine through formation of HF [9, 10, 11], thus preventing formation of PbF$_2$. The amount of water present was 1.26 the stoichiometric amount necessary to displace all the fluorine present.

Figure 6:
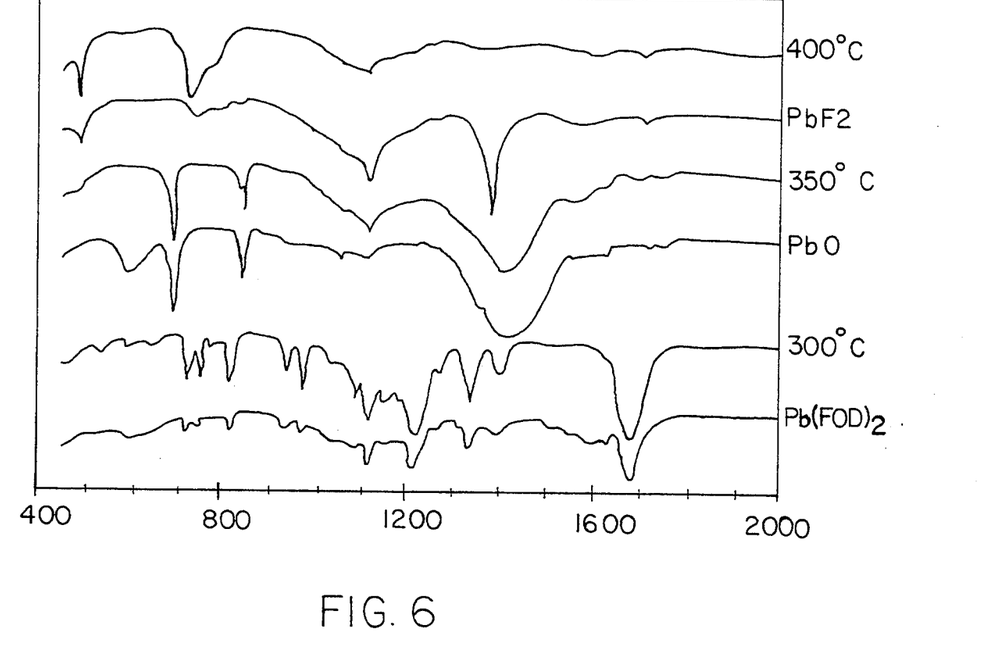
FIG. 6 is an FTIR spectra of several compound.

Products for decomposition were analyzed via Fourier Transform Infrared Spectroscopy (FTIR). FIG. 6 shows the FTIR spectra of Pb(fod)$_2$, Pb(fod)$_2$ decomposed in the presence of water and oxygen at 350° C., 400° C. and 450° C., and decomposed in the presence of water and oxygen at 350° C., 400° C. and 450° C., and PbO and PbF$_2$ standards. The product of decomposition at 300° C. has a similar spectra to that of the reference Pb(fod)$_2$; bands at 1800, 1330, 1200, 975, 925, 740, and 700 wavenumbers are present in both. This evidence suggests no decomposition has occurred at 300° C. The spectra of the product of decomposition at 350° C. closely resembles the PbO standard with identical bands at 1450, 1100, 1000, 800 and 700 wavenumbers. The similarities of these two spectra suggest that PbO has been formed at 350° C. The spectra of the decomposition products above 400° C. more closely resemble the PbF$_2$ spectra with matching bands at 1720, 710, and 500 wave numbers. This indicates that PbF$_2$ becomes the more prevalent product of decomposition above 400° C.

Figure 7:
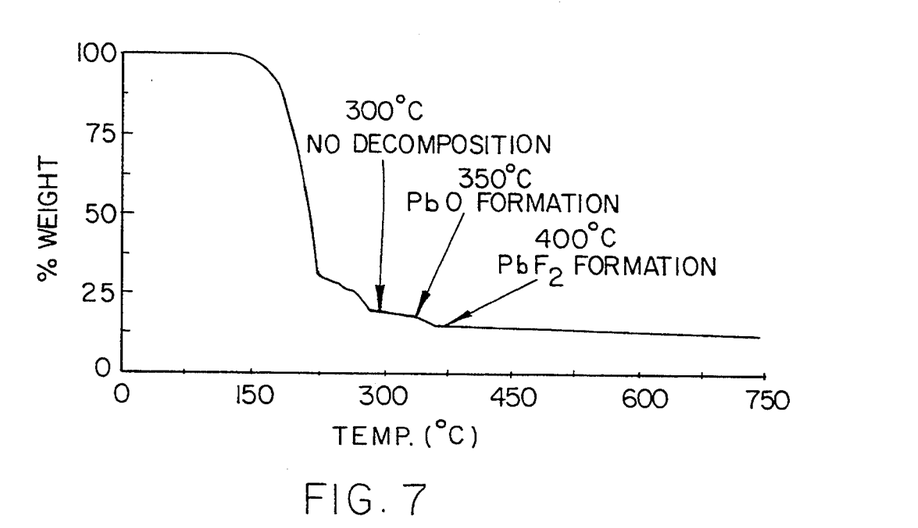
FIG. 7 is a TGA plot of Pb(fod)$_2$.

Volatility studies were carried out using thermogravimetric analysis (TGA) and mass spectroscopy. FIG. 7 shows a TGA plot of Pb(fod)$_2$ heated at 10° C./min.; percent weight loss is recorded as a function of increasing temperature. If vaporization is the only process occurring, the slope would be constant at every temperature, as it is between 150° C. and 200° C. It is important to note here that this experiment was done at 670 torr (1 atm); therefore maximum vaporization occurs at a higher temperature than the previously noted temperature of 98° C. at 1 torr. The previously discussed decomposition study suggests decomposition took place above 300° C. During decomposition, gas byproducts of the fod ligand are vaporized, and most of the lead remains in the solid phase as PbO, PbF$_2$ and other Pb-containing products of decomposition. Therefore, observed weight loss rate during decomposition is decreased relative to weight loss rate during vaporization without decomposition. At 400° C., 15-20% of the starting sample remains as decomposition products, and weight loss has ceased.

Although the decomposition studies indicated no decomposition occurs below 350° C., the TGA plot shows a decrease in rate of weight loss as low as 200° C. Several gas chromatography, mass spectral and thermal gravimetric studies on metal β-diketonate complexes have reported oligomerization as the cause of decreased volatility upon heating.

Figure 8:
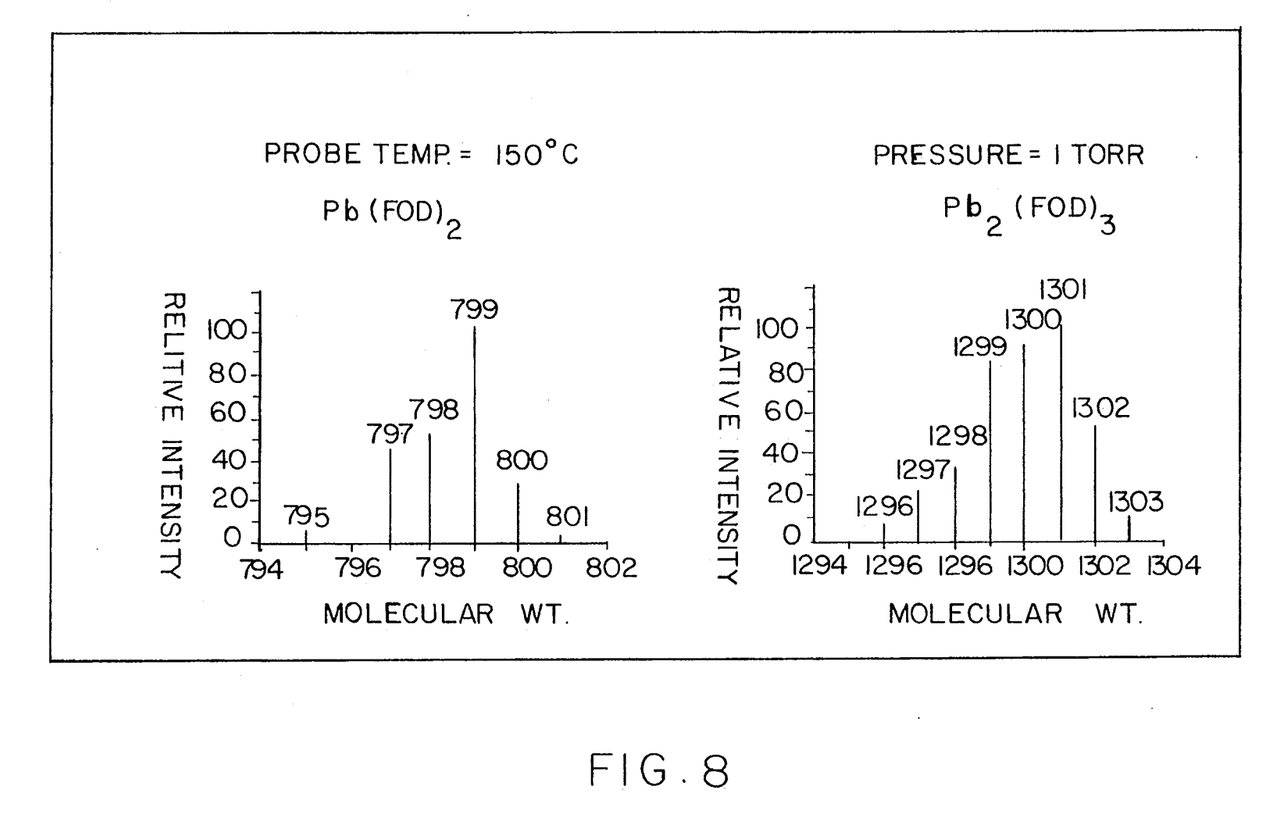
FIG. 8 is a mass spectra of synthesized and purified Pb(fod)$_2$.

FIG. 8 shows portions of a mass spectra of synthesized and purified Pb(fod)$_2$. The range of peaks centered around 797 g/mol represents the Pb(fod)$_2$ monomer. Additionally, a range of peaks around 1299 g/mol was observed, which corresponds to the oligomer Pb$_2$(fod)$_3$. The reason these species are represented by a range of peaks rather a single peak is variable weight of lead and carbon isotopes, and fragmentation and protonization of the species, caused by the chemical ionization of the mass spectral process. The formation of oligomeric species of Pb$_2$(fod)$_3$ from Pb(fod)$_2$ would decrease the vapor pressure because the concentration of higher weight, less volatile species is increased.

What is claimed is:

1. A method of producing a lead β-diketonate, comprising: combining lead oxide with a medium; subjecting the combined lead oxide and medium to ultrasonic waves, and recovering said lead β-diketonate.

2. The method of claim 1, further comprising: heating the medium in a vacuum to vaporize non-β-diketonate compounds in the medium.

3. The method of claim 1, wherein the lead oxide and medium are combined in a flask, and the step of subjecting the combined lead oxide and medium to ultrasonic waves is by placing an ultrasonic probe into the flask.

4. The method of claim 3, wherein the flask has a lower portion and an upper portion above the lower portion, and at least one conduit having one end in communication with the lower portion and another end in communication with the upper portion, and further comprising circulating the combined lead oxide and medium through the conduit while subjecting the combined lead oxide and medium to ultrasonic waves.

5. The method of claim 4, wherein the flask is immersed in a water bath, and further comprising cooling the conduit and thereby cooling the combined lead oxide and medium with the water bath while subjecting the combined lead oxide and medium to ultrasonic waves.

6. The method of claim 5, wherein the water bath is contained in a container, and further comprising flowing water through the container while subjecting the combined lead oxide and medium to ultrasonic waves.

7. The method of claim 4, wherein the circulation of the combined lead oxide and medium through the conduit is from the end in communication with the lower portion to the end in communication with the upper portion.

8. The method of claim 1, wherein the β-diketonate includes Pb(fod)$_2$ and the medium includes H-fod.

9. the method of claim 1, wherein the β-diketonate includes Pb(thd)$_2$ and the medium includes H-thd.

10. The method of claim 1, wherein the medium includes pentane.

* * * * *

UNITED STATES PATENT AND TRADEMARK OFFICE
CERTIFICATE OF CORRECTION

PATENT NO. : 5,348,631
DATED : September 20, 1994
INVENTOR(S) : Desu et al.

It is certified that error appears in the above—identified patent and that said Letters Patent is hereby corrected as shown below:

Column 3, Lines 14-26, change: " " to -- --

Column 8, Line 44, change: "the" to --The--

Signed and Sealed this

Twenty-second Day of August, 1995

Attest:

BRUCE LEHMAN

Attesting Officer

Commissioner of Patents and Trademarks